US012758521B2

(12) United States Patent
Löscher et al.

(10) Patent No.: US 12,758,521 B2
(45) Date of Patent: Oct. 13, 2026

(54) ANTIPARASITIC COMPOSITION

(71) Applicant: DERMALIQ THERAPEUTICS, INC., Wilmington, DE (US)

(72) Inventors: Frank Löscher, Schriesheim (DE); Verena Jung, Heidelberg (DE); Mikhail Barkovskiy, Heidelberg (DE); Bernhard Hauptmeier, Ingelheim-Heidenfahrt (DE); Chiara Silvana Leo, Heidelberg (DE)

(73) Assignee: DERMALIQ THERAPEUTICS, INC., Wilmington, DE (US)

( * ) Notice: Subject to any disclaimer, the term of this patent is extended or adjusted under 35 U.S.C. 154(b) by 1043 days.

(21) Appl. No.: 17/759,921

(22) PCT Filed: Feb. 6, 2021

(86) PCT No.: PCT/EP2021/052891

§ 371 (c)(1),
(2) Date: Aug. 1, 2022

(87) PCT Pub. No.: WO2021/156493

PCT Pub. Date: Aug. 12, 2021

(65) Prior Publication Data

US 2023/0066008 A1 Mar. 2, 2023

(30) Foreign Application Priority Data

Feb. 7, 2020 (EP) .................................... 20156074

(51) Int. Cl.
*A61K 31/02* (2006.01)
*A61K 9/00* (2006.01)
*A61K 31/025* (2006.01)
*A61K 31/167* (2006.01)
*A61K 31/215* (2006.01)
*A61K 31/235* (2006.01)
*A61K 31/609* (2006.01)

(52) U.S. Cl.
CPC .......... *A61K 31/235* (2013.01); *A61K 9/0014* (2013.01); *A61K 31/02* (2013.01); *A61K 31/025* (2013.01); *A61K 31/167* (2013.01); *A61K 31/215* (2013.01)

(58) Field of Classification Search
CPC ..... A61K 31/02; A61K 31/609; A61K 9/0014
See application file for complete search history.

(56) References Cited

U.S. PATENT DOCUMENTS

| | | | |
|---|---|---|---|
| 5,254,338 | A | 10/1993 | Sakai et al. |
| 5,326,566 | A | 7/1994 | Parab |
| 5,441,980 | A | 8/1995 | Fabre et al. |
| 5,518,731 | A | 5/1996 | Meadows |
| 5,667,809 | A | 9/1997 | Trevino |
| 5,851,544 | A | 12/1998 | Penska et al. |
| 5,874,469 | A | 2/1999 | Maniar et al. |
| 5,874,481 | A | 2/1999 | Weers |
| 5,904,933 | A | 5/1999 | Riess et al. |
| 5,980,936 | A | 11/1999 | Krafft et al. |
| 5,981,607 | A | 11/1999 | Ding et al. |
| 6,042,845 | A | 3/2000 | Sun et al. |
| 6,060,085 | A | 5/2000 | Osborne |
| 6,113,919 | A | 9/2000 | Cronelus |
| 6,140,374 | A | 10/2000 | May et al. |
| 6,159,977 | A | 12/2000 | Reeves |
| 6,177,477 | B1 | 1/2001 | George et al. |
| 6,224,887 | B1 | 5/2001 | Samour et al. |
| 6,262,105 | B1 | 7/2001 | Johnstone |
| 6,262,126 | B1 | 7/2001 | Meinert |
| 6,294,563 | B1 | 9/2001 | Garst |
| 6,372,243 | B2 | 4/2002 | Kobuch et al. |
| 6,391,879 | B1 | 5/2002 | Reeves |
| 6,399,087 | B1 | 6/2002 | Zhang et al. |
| 6,458,376 | B1 | 10/2002 | Meadows |
| 6,486,212 | B2 | 11/2002 | Meinert |
| 6,489,367 | B1 | 12/2002 | Meinert |
| 6,730,328 | B2 | 5/2004 | Maskiewicz |
| 7,258,869 | B1 | 8/2007 | Berry |
| 7,335,379 | B2 | 2/2008 | Carrara et al. |
| 7,740,875 | B2 | 6/2010 | Dechow |
| 8,029,977 | B2 | 10/2011 | Meinert et al. |
| 8,309,120 | B2 | 11/2012 | Koch et al. |
| 8,614,178 | B2 | 12/2013 | Theisinger et al. |
| 8,796,340 | B2 | 8/2014 | Theisinger et al. |
| 8,916,178 | B2 | 12/2014 | Krause |
| 8,986,738 | B2 | 3/2015 | Meinert |
| 9,241,900 | B2 | 1/2016 | Wilson et al. |
| 9,308,262 | B2 | 4/2016 | Günther et al. |
| 9,757,459 | B2 | 9/2017 | Günther et al. |

(Continued)

FOREIGN PATENT DOCUMENTS

| | | | |
|---|---|---|---|
| CA | 2776860 A1 * | 6/2011 | .............. A61P 43/00 |
| CA | 3112504 A1 * | 4/2020 | ............. A61K 31/02 |

(Continued)

OTHER PUBLICATIONS

Roos et al. (Pharmacotherapy of Ectoparasitic Infections, Drugs, 2001: vol. 61(8), pp. 1067-1088) (Year: 2001).*
Elkeeb, R. et al., "Transungual Drug Delivery: Current Status," International Journal of Pharmaceutics, 2010, 384:1-8.
Gehlsen et al., "A semifluorinated alkane (F4H5) as novel carrier for cyclosporine A: a promising therapeutic and prophylactic option for topical treatment of dry eye," Graefe's Arch. Clin. Exp. Ophthalmol., (2017) 255(4):767-775.
Hardung, H., "Semifluorierte und perfluorierte Vergindungen zur topischen und parenteralen Anwendung," 2008, 188 pages, retrieved from Internet, date accessed: Oct. 10, 2011, URL: <http://www.freidok.uni-freiburg.de/volltexte/5682/pdf/Dissertation_Hardung.pdf>.

(Continued)

*Primary Examiner* — Bethany P Barham
*Assistant Examiner* — Danielle Johnson
(74) *Attorney, Agent, or Firm* — Hoxie & Associates LLC

(57) ABSTRACT

The present invention relates to an antiparasitic composition comprising an antiparasitic agent and a semifluorinated alkane.

30 Claims, No Drawings

(56) References Cited

U.S. PATENT DOCUMENTS

| | | | | |
|---|---|---|---|---|
| 9,757,460 | B2 | 9/2017 | Günther et al. | |
| 9,770,508 | B2 | 9/2017 | Günther et al. | |
| 9,968,678 | B2 | 5/2018 | Theisinger et al. | |
| 10,045,996 | B2 | 8/2018 | Theisinger et al. | |
| 10,058,615 | B2 | 8/2018 | Günther et al. | |
| 10,064,944 | B2 | 9/2018 | Wilson et al. | |
| 10,130,707 | B2 | 11/2018 | Günther et al. | |
| 10,273,298 | B2 | 4/2019 | Günther et al. | |
| 10,369,117 | B2 | 8/2019 | Günther et al. | |
| 10,449,164 | B2 | 10/2019 | Günther et al. | |
| 10,507,132 | B2 | 12/2019 | Graf et al. | |
| 10,576,154 | B2 | 3/2020 | Günther et al. | |
| 10,682,315 | B2 * | 6/2020 | Scherer | A61K 9/08 |
| 10,813,976 | B2 * | 10/2020 | Löscher | A61P 27/04 |
| 10,813,999 | B2 | 10/2020 | Günther et al. | |
| 11,154,513 | B2 | 10/2021 | Scherer et al. | |
| 11,160,865 | B2 | 11/2021 | Theisinger et al. | |
| 11,273,174 | B2 * | 3/2022 | Löscher | A61P 17/10 |
| 11,357,738 | B2 * | 6/2022 | Scherer | A61F 9/0008 |
| 11,400,132 | B2 * | 8/2022 | Löscher | A61K 9/0048 |
| 11,510,855 | B2 * | 11/2022 | Löscher | A61K 8/671 |
| 11,583,513 | B2 | 2/2023 | Günther et al. | |
| 11,684,589 | B2 | 6/2023 | Günther et al. | |
| 11,844,836 | B2 | 12/2023 | Günther et al. | |
| 11,896,559 | B2 * | 2/2024 | Günther | A61K 9/0048 |
| 12,005,033 | B2 | 6/2024 | Günther et al. | |
| RE50,060 | E | 7/2024 | Graf et al. | |
| 12,029,757 | B2 * | 7/2024 | Löscher | A61K 8/375 |
| 12,128,010 | B2 * | 10/2024 | Scherer | A61K 9/08 |
| 12,150,955 | B2 * | 11/2024 | Löscher | A61P 17/02 |
| 12,226,422 | B2 * | 2/2025 | Löscher | A61K 31/5575 |
| 2002/0004063 | A1 | 1/2002 | Zhang | |
| 2002/0128527 | A1 | 9/2002 | Meinert | |
| 2002/0198266 | A1 | 12/2002 | Meinert | |
| 2003/0170194 | A1 | 9/2003 | Piotrowiak | |
| 2005/0075407 | A1 | 4/2005 | Tamarkin et al. | |
| 2005/0079210 | A1 | 4/2005 | Gupta | |
| 2006/0078577 | A1 | 4/2006 | Dechow | |
| 2006/0153905 | A1 | 7/2006 | Carrara et al. | |
| 2008/0207537 | A1 | 8/2008 | Turner et al. | |
| 2008/0260656 | A1 | 10/2008 | Mallard | |
| 2009/0104243 | A1 | 4/2009 | Utkhede et al. | |
| 2009/0169601 | A1 | 7/2009 | Koch et al. | |
| 2009/0226875 | A1 | 9/2009 | Meinert et al. | |
| 2010/0008996 | A1 | 1/2010 | Meinert | |
| 2010/0305081 | A1 | 12/2010 | Dechow | |
| 2010/0310476 | A1 | 12/2010 | Tamarkin et al. | |
| 2011/0223208 | A1 | 9/2011 | Hill et al. | |
| 2011/0269704 | A1 | 11/2011 | Seigfried | |
| 2012/0100183 | A1 | 4/2012 | Schlessinger et al. | |
| 2012/0219640 | A1 | 8/2012 | Wright | |
| 2012/0238639 | A1 | 9/2012 | Theisinger et al. | |
| 2013/0046014 | A1 | 2/2013 | Theisinger et al. | |
| 2013/0266652 | A1 | 10/2013 | Theisinger et al. | |
| 2013/0303473 | A1 | 11/2013 | Wilson | |
| 2014/0004197 | A1 | 1/2014 | Theisinger et al. | |
| 2014/0100180 | A1 | 4/2014 | Günther et al. | |
| 2014/0140942 | A1 | 5/2014 | Günther et al. | |
| 2014/0369993 | A1 | 12/2014 | Günther et al. | |
| 2015/0224064 | A1 | 8/2015 | Günther et al. | |
| 2015/0238605 | A1 | 8/2015 | Günther et al. | |
| 2016/0000941 | A1 | 1/2016 | Thorsten et al. | |
| 2016/0101178 | A1 | 4/2016 | Wilson | |
| 2016/0159902 | A1 | 6/2016 | Gunther et al. | |
| 2017/0065647 | A1 | 3/2017 | Kim et al. | |
| 2017/0087100 | A1 | 3/2017 | Scherer et al. | |
| 2017/0087101 | A1 | 3/2017 | Scherer et al. | |
| 2017/0143832 | A1 | 5/2017 | Gunther et al. | |
| 2017/0182060 | A1 | 6/2017 | Wiedersberg et al. | |
| 2017/0216204 | A1 | 8/2017 | Theisinger et al. | |
| 2018/0021434 | A1 | 1/2018 | Günther et al. | |
| 2018/0360908 | A1 | 12/2018 | Beier et al. | |
| 2019/0321218 | A1 | 10/2019 | Graf et al. | |
| 2020/0129543 | A1 | 4/2020 | Löscher et al. | |
| 2020/0188318 | A1 | 6/2020 | Günther et al. | |
| 2020/0246463 | A1 | 8/2020 | Günther et al. | |
| 2020/0268648 | A1 | 8/2020 | Günther et al. | |
| 2020/0268682 | A1 | 8/2020 | Günther et al. | |
| 2020/0338015 | A1 | 10/2020 | Scherer et al. | |
| 2021/0069014 | A1 | 3/2021 | Löscher et al. | |
| 2021/0100904 | A1 | 4/2021 | Günther et al. | |
| 2021/0106558 | A1 | 4/2021 | Löscher et al. | |
| 2021/0121471 | A1 | 4/2021 | Löscher et al. | |
| 2021/0308024 | A1 | 10/2021 | Löscher et al. | |
| 2021/0315832 | A1 | 10/2021 | Scherer et al. | |
| 2022/0031844 | A1 | 2/2022 | Mauden et al. | |
| 2022/0079980 | A1 | 3/2022 | Löscher et al. | |
| 2022/0152096 | A1 | 5/2022 | Löscher et al. | |
| 2022/0218828 | A1 | 7/2022 | Günther et al. | |

FOREIGN PATENT DOCUMENTS

| | | | | |
|---|---|---|---|---|
| CN | 103830179 | A | 6/2014 | |
| EP | 0 670 159 | | 9/1995 | |
| EP | 0965329 | A1 | 12/1999 | |
| FR | 2723291 | A1 | 2/1996 | |
| GB | 2150437 | A * | 7/1985 | A01N 25/34 |
| JP | S5721312 | A | 2/1982 | |
| JP | H0764702 | B2 | 7/1995 | |
| JP | 2001064165 | A | 3/2001 | |
| WO | 1997/012852 | A1 | 4/1997 | |
| WO | 2000/042990 | A1 | 7/2000 | |
| WO | 2011/009436 | A2 | 1/2011 | |
| WO | 2012/052418 | A1 | 4/2012 | |
| WO | 2012/093113 | A1 | 7/2012 | |
| WO | 2012/160179 | A2 | 11/2012 | |
| WO | 2012/160180 | A2 | 11/2012 | |
| WO | 2014/041055 | A1 | 3/2014 | |
| WO | 2014/041071 | A1 | 3/2014 | |
| WO | 2014/154531 | A1 | 10/2014 | |
| WO | 2017/055453 | A1 | 4/2017 | |
| WO | 2017/220625 | A1 | 12/2017 | |
| WO | WO 2018-115097 | A1 | 6/2018 | |
| WO | WO 2018-193093 | A1 | 10/2018 | |
| WO | 2019/068763 | A1 | 4/2019 | |
| WO | 2020/064549 | A1 | 4/2020 | |

OTHER PUBLICATIONS

Hardung, H., “Semifluorierte und perfluorierte Verbindungen zur topischen und parenteralen Anwendung,” 2008, English Language Abstract, 2 pages, retrieved from https://freidok.uni-freiburg.de/data/5682 (retrieved on Jul. 10, 2017).

Holm, R. et al., “A novel excipient, 1-perfluorohexyloctane shows limited utility for the oral delivery of poorly water-soluble drugs,” European Journal of Pharmaceutical Sciences, 2011, 42: 416-422.

Mantle et al., “Adverse and beneficial effects of plant extracts on skin and skin disorders,” Adverse Drug Reaction and Toxicological Reviews, 2001, 20(2): 89-103.

Meinert, H. et al., “The Use of Semifluorinated Alkanes in Blood-Substitutes,” Biomaterials, Artificial Cells, and Immobilization Biotechnology, 1993, 21 (5), 583-595.

Meinert, H. et al., “Semifluorinated Alkanes—A New Class of Compounds with Outstanding Properties for Use in Ophthalmology,” European Journal of Ophthalmology, 2000, 10 (3), 189-197.

Murdan, S., “Enhancing the Nail Permeability of Topically Applied Drugs,” Expert Opinion on Drug Delivery, 2008, 5 (11):1267-1282.

Karabela et al., “Treatment of Phthiriasis Palpebrarum and Crab Louse: Petrolatum Jelly and 1% Permethrin Shampoo,” Case Reports in Medicine, vol. 2015, No. 287906, 4 pages, (2015).

Padzik et al., “Effect of Povidone Iodine, Chlorhexidine Digluconate and Toyocamycin on Amphizoic Amoebic Strains, Infectious Agents of *Acanthamoeba* keratitis—a growing threat to human health worldwide,” Annals of Agricultural and Environmental Medicine, vol. 25, No. 4, p. 725-731, (2018).

“Semifluorinated alkane technology brings advantages for topical therapy,” Ophthalmology Times, 2016, pp. 1-2.

Bertilla, S. et al., “Semifluorinated Alkanes as Stabilizing Agents of Fluorocarbon Emulsions,” Springer, vol. 12, 24 pages, (2005).

(56) References Cited

OTHER PUBLICATIONS

Dutescu, R. et al., "Semifluorinated alkanes as a liquid drug carrier system for topical ocular drug delivery." European Journal of Pharmaceutics and Biopharmaceutics, vol. 88, No. 1, pp. 123-128, (2014).

Freiburger Dokumentenserver (FreiDok), Albert-Ludwigs-Unversität Freiburg, retrieved from http://www.freidok.uni-freiburg.de/volltexte/5682/, retrieved on Feb. 5, 2014, 2 pages, English abstract included.

JPH0764702b2, Kanebo Ltd, "Cosmetic of Polyphasic Emulsion Type," Jul. 12, 1995, English language machine translation of abstract, Espacenet, date obtained: Apr. 30, 2021, 1 page <https://worldwide.espacenet.com/patent/search/family/014142733/publication/JPH0764702B2?q=JPH0764702B2>.

JPS5721312a, Green Cross Corp, "Breathable Ointment," Feb. 2, 1982, English language machine translation of abstract, Espacenet, date obtained: Apr. 30, 2021, 1 page <https://worldwide.espacenet.com/patent/search/family/014132731/publication/JPS5721312A?q=JPS5721312A>.

Singh, P. et al. "Pilosebaceous Unit: Anatomical Considerations and Drug Delivery Opportunities," Indian Journal of Pharmacology, vol. 32, pp. 269-281, (2000), 13 pages.

* cited by examiner

ANTIPARASITIC COMPOSITION

CROSS-REFERENCE TO RELATED APPLICATIONS

This application is national stage application filed under 35 U.S.C. § 371 of International Application No. PCT/EP2021/052891, filed on Feb. 6, 2021, which claims priority to and the benefit of European Application No. 20156074.5, filed on Feb. 7, 2020, the contents of each of which are hereby incorporated by reference in their entireties.

The present invention relates to compositions and methods that can be used in the treatment of parasitic infestations, in particular ectoparasitic infestations of the skin.

BACKGROUND OF THE INVENTION

The term infestation refers to parasitic diseases caused by animals such as arthropods (i.e. mites, ticks, and lice) and worms. An ectoparasitic infestation is a parasitic disease caused by organisms that live primarily on the surface of the host. Examples of ectoparasitic infestations are scabies, body lice, head lice, ticks and fleas.

Mites are among the smallest arthropods. The majority of mite species are harmless to humans or domestic animals, but a few species can colonise mammals and cause allergenic diseases. Many types of itchy skin rashes are caused by mites. Among these, scabies is caused by the parasitic mite *Sarcoptes scabiei*. Scabies is a contagious infestation transmitted by skin to skin contact and sometimes by contact with contaminated material. Scabies is transmitted by the female scabies mite, which burrows into the top layer of the epidermis to lay eggs, before dying 30 to 60 days later. If infestation occurs, the first papules appear within 2 to 5 weeks. The main symptom of scabies is a severe itch, which becomes particularly severe at night. Preferred regions of infestation are the areas where the skin is thin (Deutsches Ärzteblatt International 2016; 113:757-62/Supplementary material).

As the mites are localised in the stratum corneum, in the majority of the cases it is sufficient a topical treatment with an antiscabies to kill the mites, the larves and the eggs. One of the drugs of choice for the treatment of scabies is permethrin, as it is effective against different kinds of scabies independently from the age of the patients. On the market a cream 5% permethrin is available. The 5% permethrin cream contains 0.45 g benzyl alcohol per tube, which may cause allergic reactions, such as allergic contact dermatitis. Permethrin is also available in the market as a solution InfectoPedicul® 430 mg/100 ml for a one time treatment of the hair in case of head louses. The solution comprises among others ethanol 96%, 2-propanol and water.

Crotamiton is a scabicidal and antipruritic agent available as a cream or lotion for topical use only. It is a colorless to slightly yellowish oil, having a faint amine-like odor. It is miscible with alcohol and with methanol. Crotamiton is toxic to the scabies mite. Crotamiton is available as 10% lotion, cream and ointment as well as a 5% gel. The treatment requires 3 to 5 days to be effective.

Benzylbenzoate represents another option for treatment of scabies. This substance presents a good acaricide and ovocide effect. Commercial products containing benzylbenzoate comprise with propyleneglycol and cetylstearylalcohol potential contactallergenes. Available is an emulsion of benzylbenzoate in two concentrations 25% and 10% (Antiscabiosum®). The emulsion is applied for three consecutive days on the skin and only on the fourth day it can be removed by showering.

*Demodex* is a genus of tiny mites that live in or near hair follicles of mammals. Two species live on humans: *Demodex folliculorum* and *Demodex brevis*, both frequently referred to as eyelash mites. Both species are primarily found in the face, near the nose, the eyelashes, and eyebrows, but also occur elsewhere on the body. The mites may be eradicated with topical insecticides such as crotamiton cream, permethrin cream, ivermectin cream, and also with topical or systemic metronidazole.

Lice are barely visible wingless insects that infest the head, body, or pubic area and live by sucking blood. They spread easily from person to person by close contact and shared clothing and other personal items. Head lice and pubic lice live directly on the person, whereas body lice live on clothing and bedding.

To treat head lice non-prescription shampoos and creams containing pyrethrins plus piperonyl butoxide are applied for 10 minutes and are then rinsed out. Prescription permethrin (a synthetic form of pyrethrin), applied as a liquid or as a cream, is also effective. Lindane as a prescription drug can be applied as a lotion or shampoo. It also cures lice infestation but is not as effective as the other preparations.

All of these louse treatments are repeated in 7 to 10 days to kill newly hatched lice. Lice have started to become resistant to drugs and may be hard to kill. One dose of the drug ivermectin is usually given by mouth if lice resist standard treatment. Lice that affect the eyelashes can be treated with petroleum jelly applied for 8 to 10 days, fluorescein eye drops, ivermectin taken by mouth, petrolatum salve, physostigmine ointment, or careful removal of each louse with an instrument.

One of the disadvantages of the commercial antiparasitic compositions is that they comprise alcohol which causes additional irritation and pain to the skin, in particular in presence of lesions.

The majority of commercial antiparasitic compositions are semisolid formulation in form of gels, ointments or creams which are difficult to uniformly distribute over large areas of the skin or body surface and which are not self-spreading into difficult to reach areas of the body such as the back and skin folds. For example, scabies patients need to be hospitalized because it is impossible with existing products to self-treat large areas of the skin, such as the whole body surface.

EP2286663B1 describes alcohol free compositions comprising isopropyl myristate for use in methods of killing ectoparasites on a subject.

SUMMARY OF THE INVENTION

The objective of the present invention is to provide an antiparasitic composition for topical application to the skin of a subject and which may be used to treat parasitic infestations such as scabies, louses and ticks.

The object of the present invention is attained according to the claims. The present invention provides an antiparasitic composition comprising an antiparasitic agent and a semifluorinated alkane.

In a second aspect, the present invention provides an antiparasitic composition comprising an antiparasitic agent and a semifluorinated alkane for use as a medicament, particularly for use in a method of treating a parasitic infestation.

In a third aspect, provided is also a method of topical application of an antiparasitic composition comprising applying with a wipe, a roll-on dispenser or a spray dispenser, an antiparasitic composition comprising an antiparasitic agent and a semifluorinated alkane.

In a fourth aspect, provided is a method of treating a parasitic infestation comprising topically applying an antiparasitic composition comprising an antiparasitic agent and a semifluorinated alkane to the skin of a subject in need thereof.

In a fifth aspect, the present invention provides a kit comprising a) an antiparasitic composition comprising an antiparasitic agent and a semifluorinated alkane and b) a dispenser selected from a roll-on dispenser, a spray dispenser and a wipe.

The present inventors have found that an antiparasitic composition can be obtained by mixing an antiparasitic agent and a semifluorinated alkane. Said composition has the advantages of being free of alcohol, of being easy to spread on the skin, for example through a non-touch application using a roll-on dispenser, a wet wipe or a spray dispenser, therefore simplifying the application process to the skin of a subject. The composition of the present invention has the further advantage of not leaving greasy residues on the skin.

The composition of the present invention has the further advantage of allowing coverage of great or small areas of the skin easily and in a short time when applied through a roll-on dispenser or a spray dispenser or a wet wipe. The compositions of the present invention are characterized as being self-spreading, allowing coverage of difficult to reach areas such as the back or skin folds, easily and in a short time when applied through a non-touch application utilizing a spray dispenser, or a roll-on dispenser or a wet wipe.

The composition of the present invention is water-free and do not require preservatives, surfactants or additional penetration enhancers, all of which can lead to pain in inflamed skin and local tolerability issues during short- and long-term use.

The composition of the present invention can be differentiated from any cream, ointment or foam by the case of application and improved cutaneous safety, especially when applied in sensitive or hard-to-treat areas such as the scalp, face, intertriginous, genitals, nails, hands and feet. It will be delivered as liquids using special containers designed for non-touch application. There will be no need to rub or massage the composition into the skin and it will be possible to put on clothing shortly after application of the composition without a long wait period for absorption into the skin. There will be no staining of fabrics, such as clothing, or bed sheets/pillows.

DETAILED DESCRIPTION OF THE INVENTION

The present invention provides an antiparasitic composition comprising an antiparasitic agent and a semifluorinated alkane.

An antiparasitic agent is a drug used to treat parasitic diseases, such as those caused for example by ectoparasites and parasitic fungi. In a preferred embodiment of the present invention, the antiparasitic agent is an ectoparasiticidal agent. An ectoparasiticide is an antiparasitic drug used in the treatment of ectoparasitic infestations, that is drugs used to kill the parasites that live on the body surface. Preferably, the antiparasitic agent is an ectoparasiticide selected from the group consisting of a pyrethroid, pyrethrins, an anilide, a benzoate, more preferably a pyrethroid, a benzoate or an anilide, most preferably a pyrethroid or an anilide.

Anilides (or phenylamides) are a class of chemical compounds which are acyl derivatives of aniline. Pyrethroids are synthetic chemical insecticides whose chemical structures are adapted from the chemical structures of the pyrethrins, which are botanical insecticides derived from *chrysanthemum* flowers.

In a preferred embodiment, the antiparasitic agent is selected from permethrin, benzyl benzoate, and crotamiton. More preferably, the antiparasitic agent is selected from permethrin and crotamiton, most preferably permethrin.

In a further preferred embodiment, the antiparasitic agent is selected from permethrin, benzyl benzoate, crotamiton, ivermectin and lindane.

The antiparasitic agent may be present at a concentration of up to 10% w/v, preferably of up to 5% w/v with respect to the total volume of the composition. In a preferred embodiment, the antiparasitic agent is present at a concentration of from 0.5% w/v to 10% w/v, preferably of from 0.5% w/v to 5% w/v with respect to the total volume of the composition. In a further preferred embodiment, the antiparasitic agent is present at a concentration of from 0.5% w/v to 1.5% w/v, preferably at a concentration of about 1% w/v with respect to the total volume of the composition.

Unless otherwise indicated, the term "% w/v" as used throughout herein in connection with the present composition denotes the amount of a component of a composition (such as, for example, the antiparasitic agent) as a weight percentage in relation to the total volume of the composition (with 'w' denoting the weight and 'v' denoting volume). For example, 0.05% (w/v) may be understood as relating to 0.5 mg of a component in 1 mL of the composition, and 0.1% (w/v) would correspond to 1.0 mg of a component in 1 mL of the composition.

The term "semifluorinated alkane", also referred to as "SFA" throughout this document, as used herein refers to a linear or branched compound composed of at least one perfluorinated segment (F-segment) and at least one non-fluorinated hydrocarbon segment (H-segment). Preferably, the semifluorinated alkane is a linear or branched compound composed of one perfluorinated segment (F-segment) and one non-fluorinated hydrocarbon segment (H-segment). Preferably, said semifluorinated alkane is a compound that exists in a liquid state within the temperature range of 4° to 40° C.

It is preferred that the F- and the H-segment of the linear or branched semifluorinated alkane comprise, independently from one another, 2 to 10 carbon atoms. According to a preferred embodiment of the present invention, the semifluorinated alkane is a linear compound of the formula (F(CF2)n(CH2)mH, wherein n and m are integers independently selected from each other from the range of 2 to 10.

According to another nomenclature, the linear semifluorinated alkane may be referred to as FnHm, wherein F means the perfluorinated hydrocarbon segment, H means the non-fluorinated hydrocarbon segment and n, m is the number of carbon atoms of the respective segment. For example, F4H5 is used for 1-perfluorobutyl-pentane. In a preferred embodiment of the present invention, the semifluorinated alkane is a semifluorinated alkane of formula F(CF2)n(CH2)mH wherein n is selected from 4 to 6 and m is selected from 5 to 10. More preferred is a semifluorinated alkane selected from the group consisting of F4H5, F4H6, F4H8, F4H10, F6H6, F6H8, F8H8, F6H10. Most preferred is a semifluorinated alkane selected from F4H8, F4H5, F6H6 and F6H8, or the semifluorinated alkane is F6H8. Also preferred is a semifluorinated alkane selected from the group consisting of F4H4, F4H5, F4H6, F4H8, F4H10, F6H2, F6H4, F6H6, F6H8, F8H8, F6H10.

In the present invention the composition may comprise a semifluorinated alkane in an amount of from about 75% (w/w) to about 99% (w/w), more preferably from about 90% (w/w) to about 99% (w/w) with respect to the total weight of the composition. In a most preferred embodiment of the present invention, the composition comprises a semifluorinated alkane in an amount of at least 75% w/w, preferably at least 85% w/w, more preferably at least 90% w/w with respect to the total weight of the composition.

The term "spreading" or "spreadability", as used herein refers to the characteristic of a composition to allow for distribution of the composition on the skin. Spreadability is related to the contact angle of the drop of a liquid or a semisolid composition on a standardized substrate and is a measure of lubricity, which is directly related to the coefficient of friction. The efficacy of a topical therapy depends on the patient spreading the drug composition in an uniform layer to administer a standard dose. Spreadability is therefore an important characteristic of these compositions and is responsible for correct dosage transfer to the target site, ease of application on the substrate, and most important, consumer preference. The antiparasitic compositions of the present invention exhibit excellent spreading characteristics and are thus especially suited for administration to sensitive or difficult to reach areas of the body or the skin and/or for non-touch application to the skin.

In the present invention the composition may comprise more than a single semifluorinated alkane, preferably the composition may comprise a mixture of at least two semifluorinated alkanes, more preferably the composition may comprise a mixture of at least two semifluorinated alkanes, wherein at least one is characterized by a vapor pressure of at least 2, more preferably of at least 4, event more preferably of at least 10 mmHg at 25° C.; thus allowing for rapid evaporation of said semifluorinated alkane upon administration to the skin. Preferably, the antiparasitic composition may comprise a mixture of at least two semifluorinated alkanes, wherein the semifluorinated alkane allowing for rapid evaporation upon administration to the skin is selected from F6H2, F4H4 or F4H5, preferably said semifluorinated alkane is F6H2.

In a preferred embodiment, the composition of the present invention is a liquid or semisolid composition, that is the antiparasitic agent is dissolved or suspended in the semifluorinated alkane. In a most preferred embodiment, the composition of the present invention is a solution, such as a liquid solution or a semisolid solution.

In an embodiment, the present invention relates to an antiparasitic composition comprising an antiparasitic agent dissolved in a vehicle comprising a semifluorinated alkane. Preferably, the antiparasitic composition comprises an antiparasitic agent dissolved in a vehicle comprising a semifluorinated alkane, and optionally one or more excipients. More preferably, the antiparasitic composition comprises an antiparasitic agent dissolved in a vehicle comprising a semifluorinated alkane, and optionally one or more excipients selected from the group of oily excipients and cosolvents.

The antiparasitic composition of the present invention is preferably formulated as a solution, thus allowing application of the composition to the skin with for example a wet wipe, a roll-on dispenser or a spray dispenser. A wet wipe may comprise a substrate like a nonwoven material impregnated with the antiparasitic composition. The wet wipe is particularly useful in cases in which the area to be treated is small, such as the face, the scalp, the area around the eyes, the eyebrows, the eyelashes.

Alternatively, the antiparasitic composition of the present invention may be placed in a dispenser like a roll-on dispenser or a spray dispenser or a dropper. The application of the antiparasitic composition of the present invention through a roll-on dispenser or a spray dispenser, may result useful in cases where the entire body or large areas of the body have to be treated as well as in cases where localized administration to small areas of the skin for example is required. A dropper may be utilized for localized administration to smaller areas of the skin.

Preferably, the composition of the present invention is in the form of a wet wipe, a roll-on or a spray composition. Herein, a composition in form of a wet wipe, a roll-on or a spray, relates to a composition that is formulated in such way that it is suitable to be used or contained in devices, such as a wet wipe, a roll-on dispenser or a spray dispenser. More preferably, the composition of the present invention is in the form of a roll-on or spray composition. Even more preferably, the composition of the present invention is in form of a spray composition.

Preferably, the composition of the present invention is provided in a form to allow for a non-touch application, namely that application onto the skin, as well as administration into the skin is performed without contacting the target skin area. Thus, the composition of the present invention is provided in a form to allow for a non-touch application, namely in form of a spray, a roll-on, a dropper bottle or a wet wipe. Herein, a composition in form of a spray, a roll-on, a dropper or a wet wipe, relates to a composition that is formulated in such way that it is suitable for non-touch application to be used or contained in devices, such as a spray dispenser, a roll-on dispenser, a dropper bottle or a wet wipe packed in a pouch. More preferably, the antiparasitic composition for non-touch application of the present invention is in the form of spray composition or a roll-on. Even more preferably, the antiparasitic composition for non-touch application of the present invention is in form of a spray composition.

The antiparasitic composition of the present invention are water-free and do not require pharmaceutical ingredients selected from preservatives, surfactants or penetration enhancers. Thus, the antiparasitic composition of the present invention is water-free and is preferably free of preservatives, surfactants and/or penetration enhancers.

In a preferred embodiment, the antiparasitic composition is a liquid composition that is topically administrable, preferably by non-touch application to large areas of the skin utilizing only small volumes of the composition to distribute the antiparasitic agent uniformly on the target site or area. Herein, the present invention takes advantage of the superior spreading capabilities of the semifluorinated alkanes that allow for uniform coverage of more than 0.5 cm2 of the skin target area per microliter composition, when applied as a droplet. Utilizing roll-on dispensers or spray dispenser, thus applying the composition by non-touch application to the target skin area, the antiparasitic composition of the present invention allows for uniform coverage of even larger target areas of the skin, for example uniform coverage of more than 0.5, 1, 2, 3, 4, 5, 10, 15 cm2 of the target skin area per microliter composition.

The antiparasitic composition of the present invention is preferably free of alcohol. The absence of alcohol constitutes a further advantage of the composition of the present invention, since alcohol causes further irritation or allergic reactions to the skin. In a preferred embodiment, the composition of the present invention is free of alcohol and/or preservative and/or water. In a preferred embodiment, the antiparasitic composition of the present invention is free of water, alcohol and preservatives.

The composition of the present invention may also comprise one or more further excipients as an additional component. The term "excipients" as used herein refers to any pharmaceutically acceptable natural or synthetic substance that may be added to the composition of the present invention. The present composition may comprise one or more excipients such as, for example, an antioxidant, a preservative, a lipid or oily excipient, a cosolvent, a wax, a surfactant or a lubricant or a combination thereof.

Suitable antioxidants which may be employed comprise, for example: butylated hydroxytoluene (BHT), butylated hydroxyanisole (BHA), tertiary butylhydroquinone (TBHQ), vitamin E, vitamin E derivatives (i.e. alpha-tocopherol acetate) and/or ascorbic acid or derivatives thereof.

Suitable oily excipients which may be added in the composition of the present invention comprise, for example, vegetable oils (i.e. soybean oil, olive oil, sesame oil, cotton seed oil, castor oil, sweet almond oil), mineral oil (i.e. petrolatum and liquid paraffin), medium chain triglycerides (MCT), oily fatty acids, squalane, squalene, essential oils, silicone oils, isopropyl myristate, oily fatty alcohols, esters of sorbitol and fatty acids, oily sucrose esters, or any other oily substance which is physiologically tolerated by the skin. In a preferred embodiment, the composition of the present invention comprises an oily excipient selected from squalane, silicone oils, mineral oils, essential oils, liquid triglycerides, medium chain tryglicerides, vegetable oils; preferably squalane, paraffin oil, medium chain tryglicerides.

Examples of cosolvents which may be included in the antiparasitic composition are isopropanol, ethanol, liquid medium chain triglycerides, N-methyl-2-pyrrolidone, diethylene glycol monomethylether, diethylene glycol monoethylether, ethyl acetate, ethyl oleate, octyldodecanol, diethyl sebacate. Preferably, the cosolvent is selected from isopropanol, ethanol, liquid medium chain triglycerides, diethylene glycol monoethylether, diethyl sebacate.

Example of waxes, which may be included in the antiparasitic composition are plant waxes, animal waxes or petroleum derived waxes.

In a preferred embodiment, the composition of the present invention further comprises an oily excipient, preferably an oily excipient selected from squalane, mineral oil and medium chain tryglicerides. The oily excipient may be present in an amount of from 0 to 25% w/w, preferably of from 0 to 10% w/w, more preferably of from 0 to 5% w/w with respect to the total weight of the composition. Preferably the composition according to the invention further comprises an oily excipient selected from squalane, paraffin oil and medium chain tryglicerides at a concentration of from 0 to 25% w/w, more preferably of from 0 to 10% w/w, most preferably of from 0 to 5% w/w with respect to the total weight of the composition.

In a further preferred embodiment, the antiparasitic composition comprises ivermectin, a semifluorinated alkane and a cosolvent, more preferably the composition comprises ivermectin, a semifluorinated alkane and an alcohol, such as ethanol or isopropanol.

In a preferred embodiment, the antiparasitic composition of the present invention comprises or consist of 0.1% w/v to 5% w/v permethrin dissolved in a vehicle comprising F6H8, and optionally one or more excipients selected from the group of cosolvents and/or oily excipients, or comprises or consist of 0.5% w/v permethrin dissolved in a vehicle comprising F6H8, and optionally one or more excipients selected from the group of cosolvents and/or oily excipients, or comprises or consist of 0.1% w/v to 5% w/v crotamiton dissolved in a vehicle comprising F6H8, and optionally one or more excipients selected from the group of cosolvents and/or oily excipients, or comprises or consist of 1% w/v crotamiton dissolved in a vehicle comprising F6H8, and optionally one or more excipients selected from the group of cosolvents and/or oily excipients, or comprises 0.1% w/v to 5% w/v ivermectin dissolved in a vehicle comprising F6H8, and optionally one or more excipients selected from the group of cosolvents and/or oily excipients, or comprises or consist of 1% w/v ivermectin dissolved in a vehicle comprising F6H8, and optionally one or more excipients selected from the group of cosolvents and/or oily excipients In a further preferred embodiment, the antiparasitic composition of the present invention is a topically administrable liquid composition, that comprises or consist of 0.1% w/v to 5% w/v permethrin dissolved in a vehicle comprising F6H8, and optionally one or more excipients selected from the group of cosolvents and/or oily excipients, or that comprises or consist of 0.5% w/v permethrin dissolved in a vehicle comprising F6H8, and optionally one or more excipients selected from the group of cosolvents and/or oily excipients, or that comprises or consist of 0.1% w/v to 5% w/v crotamiton dissolved in a vehicle comprising F6H8, and optionally one or more excipients selected from the group of cosolvents and/or oily excipients, or that comprises or consist of 1% w/v crotamiton dissolved in a vehicle comprising F6H8, and optionally one or more excipients selected from the group of cosolvents and/or oily excipients, or that comprises 0.1% w/v to 5% w/v ivermectin dissolved in a vehicle comprising F6H8, and optionally one or more excipients selected from the group of cosolvents and/or oily excipients, or that comprises or consist of 1% w/v ivermectin dissolved in a vehicle comprising F6H8, and optionally one or more excipients selected from the group of cosolvents and/or oily excipients, and wherein the composition is configured (or is effective) to cover area of the skin of at least 0.5 cm2 per microliter when applied by non-touch application.

In a second aspect, the present invention provides an antiparasitic composition comprising an antiparasitic agent and a semifluorinated alkane for use as a medicament, particularly for use in a method of treating a parasitic infestation. Preferably, the parasitic infestation is an ectoparasitic infestation, more preferably a mite infestation or a lice infestation, most preferably an infestation selected from scabies, head lice infestation, body lice infestation, mite infestation of the eyelashes and of the eyebrows (such as infestations by *demodex* mites), lice infestation of the eyelashes and of the eyebrows. Also preferably, the parasitic infestation is selected from scabies, head lice infestation, body lice infestation, lice infestation of the eyelashes and of the eyebrows, mite infestations of the eyelashes and of the eyebrows, tick infestations, fleas infestations In a further preferred embodiment, the parasitic infestation is related or caused by scabies, head lice, body lice, lice of the eyelashes, lice of the eyebrows, mites of the eyelashes (*demodex*), mites of the eyebrows, ticks or fleas.

All the embodiments described above in connection with the first aspect of the invention apply to the antiparasitic composition for use as a medicament and for use in a method of treating a parasitic infestation, respectively.

In a third aspect, provided is also a method of topical application of an antiparasitic composition comprising applying with a wipe, a roll-on dispenser or a spray dispenser, an antiparasitic composition comprising an antiparasitic agent and a semifluorinated alkane. Preferably the method is applied to the skin of a subject in need thereof.

Unless otherwise indicated, a roll-on or roll-on dispenser as used in the present invention means a dispensing device comprising a container with a moving applicator ball mounted thereon, used for storing and application of a composition, contained in the container, to the body of a subject or onto any other surfaces. A spray dispenser as used herein means a dispensing device that turns a liquid into a fine mist, such as a spray bottle with a pump. A wipe or a wet wipe as used herein means a moist cloth.

All the embodiments described above in connection with the first aspect of the invention apply to the method of topical application of an antiparasitic composition of the third aspect of the invention In a fourth aspect, provided is a method of treating a parasitic infestation comprising topically applying an antiparasitic composition comprising an antiparasitic agent and a semifluorinated alkane to the skin of a subject in need thereof. In a preferred embodiment, the method of treating a parasitic infestation comprises the step of applying the antiparasitic composition of the present invention to the skin of a subject in need thereof with a roll-on dispenser, a spray dispenser or a wipe. In a more preferred embodiment, the method of treating a parasitic infestation comprises the step of applying the antiparasitic composition of the present invention to the skin of a subject in need thereof through a roll-on dispenser, a spray dispenser with a pump or a wipe.

Preferably, the parasitic infestation is an ectoparasitic infestation, more preferably a mite infestation or a lice infestation, most preferably an infestation selected from scabies, head lice infestation, body lice infestation, mite infestation of the eyelashes and of the eyebrows (such as infestations by *demodex* mites), lice infestation of the eyelashes and of the eyebrows.

All the embodiments described above in connection with the first aspect of the invention apply to the method of treating a parasitic infestation of the fourth aspect of the invention.

In a fifth aspect, the present invention provides a kit comprising a) an antiparasitic composition comprising an antiparasitic agent and a semifluorinated alkane and b) a dispenser selected from a roll-on dispenser, a spray dispenser and a wipe.

All the embodiments described above in connection with the first aspect of the invention apply to the kit of the fifth aspect of the invention.

The followings are numbered items comprised by the present invention:

1. An antiparasitic composition comprising an antiparasitic agent and a semifluorinated alkane.
2. The antiparasitic composition of item 1 in form of a liquid or a semisolid composition, preferably the composition is a liquid solution.
3. The antiparasitic composition of any of the preceding items, wherein the antiparasitic agent is an ectoparasiticide.
4. The antiparasitic composition of any of the preceding items wherein the antiparasitic agent is one selected from the group consisting of a pyrethroid, a pyrethrin, an anilide, a benzoate.
5. The antiparasitic composition of any of the preceding items wherein the antiparasitic agent is selected from the group consisting of a pyrethroid, a benzoate or an anilide,
6. The antiparasitic composition of any of the preceding items wherein the antiparasitic agent is selected from the group consisting of a pyrethroid or an anilide.
7. The antiparasitic composition of any of the preceding items wherein the antiparasitic agent is selected from permethrin, crotamiton and benzylbenzoate, or wherein the antiparasitic agent is selected from permethrin, crotamiton, benzylbenzoate. ivermectin and lindane
8. The antiparasitic composition of any of the preceding items, wherein the semifluorinated alkane is of generic formula F(CF2)n(CH2)mH, wherein n and m are integers independently selected from each other from the range of 2 to 10.
9. The antiparasitic composition of any of the preceding items, wherein the semifluorinated alkane is of formula F(CF2)n(CH2)mH wherein n is selected from 4 to 6 and m is selected from 5 to 10.
10. The antiparasitic composition of any of the preceding items, wherein the semifluorinated alkane is selected from the group consisting of F4H5, F4H6, F4H8, F4H10, F6H6, F6H8, F8H8, F6H10, or is selected from the group consisting of F4H4, F4H5, F4H6, F4H8, F4H10, F6H2, F6H4, F6H6, F6H8, F8H8, F6H10.
11. The antiparasitic composition of any of the preceding items, wherein the semifluorinated alkane is selected from F4H8, F4H5, F6H6 and F6H8.
12. The antiparasitic composition of any of the preceding items, wherein the semifluorinated alkane is selected from F4H8, F6H6 and F6H8.
13. The antiparasitic composition of any of the preceding items, wherein the semifluorinated alkane is F6H8.
14. The antiparasitic composition of any of the preceding items, wherein the antiparasitic agent is present at a concentration of from 0.5% w/v to 10% w/v with respect to the total volume of the composition.
15. The antiparasitic composition of any of the preceding items, wherein the antiparasitic agent is present at a concentration of from 0.5% w/v to 5% w/v with respect to the total volume of the composition.
16. The antiparasitic composition of any of the preceding items, wherein the composition further comprises an oily excipient.
17. The antiparasitic composition of any of the preceding items, wherein the composition further comprises an oily excipient selected from squalane, silicone oils, mineral oils, essential oils, liquid triglycerides, medium chain tryglicerides, vegetable oils.
18. The antiparasitic composition of any of the preceding items, further comprising an oily excipient selected from squalane, paraffin oil, medium chain tryglicerides.
19. The antiparasitic composition of any of the preceding item further comprising squalane.
20. The antiparasitic composition of any of items 16 to 19, wherein the oily excipient is present at a concentration of from 0 to 25% w/w with respect to the total weight of the composition.

21. The antiparasitic composition of item 20, wherein the oily excipient is present at a concentration of from 0 to 10% w/w with respect to the total weight of the composition.
22. The antiparasitic composition of any of items 1 to 15 wherein the composition consists of an antiparasitic agent and a semifluorinated alkane.
23. The antiparasitic composition of any of items 1 to 21, wherein the composition consists of an antiparasitic agent, a semifluorinated alkane and an oily excipient, or wherein the composition consists of an antiparasitic agent, a semifluorinated alkane and a cosolvent.
24. The antiparasitic composition of any of the preceding items, wherein the composition is free of alcohol.
25. The antiparasitic composition of any of the preceding items, wherein the composition is free of water.
26. The antiparasitic composition of any of the preceding items, wherein the composition is free of preservatives.
27. The antiparasitic composition according to any of the preceding items in the form of a wet wipe, a roll-on or a spray composition, or wherein the composition is provided in a dropper.
28. The antiparasitic composition as defined in any of the preceding items, for use as a medicament.
29. The antiparasitic composition as defined in any of the preceding items for use in a method of treating a parasitic infestation.
30. The antiparasitic composition for the use of item 29, wherein the parasitic infestation is selected from a mite infestation and a lice infestation, or wherein the parasitic infestation is related or caused by scabies, head lice, body lice, lice of the eyelashes, lice of the eyebrows, mites of the eyelashes (*demodex*), mites of the eyebrows, ticks or fleas.
31. The antiparasitic composition for the use of item 30, wherein the parasitic infestation is selected from scabies, head lice infestation, body lice infestation, lice infestation of the eyelashes and of the eyebrows, mite infestations of the eyelashes and of the eyebrows, tick infestations, fleas infestations.
32. The antiparasitic composition for the use of item 31, wherein the parasitic infestation is scabies.
33. The antiparasitic composition for the use of any of items 29 to 32, wherein the antiparasitic agent is permethrin.
34. A method of topical application of an antiparasitic composition comprising applying with a wipe, a roll-on dispenser or a spray dispenser an antiparasitic composition as defined in any of items 1 to 27.
35. A method of treating a parasitic infestation comprising topically applying an antiparasitic composition as defined in any of items 1 to 27 to the skin of a subject in need thereof or to a surface contaminated by parasites.
36. The method according to item 35, wherein the antiparasitic composition is applied with a roll-on dispenser, a spray dispenser or a wipe.
37. A kit comprising a) an antiparasitic composition according to any of items 1-27, b) a wipe, a spray dispenser or a roll-on dispenser.
38. A kit according to item 37, further comprising instructions for use.
39. The antiparasitic composition according to items 1 to 27, comprising of consisting of 0.1% w/v to 5% w/v permethrin, F6H8, and optionally one or more excipients selected from the group of cosolvents and/or oily excipients.
40. The antiparasitic composition according to items 1 to 27, comprising of consisting of 0.1% w/v to 5% w/v crotamiton, F6H8, and optionally one or more excipients selected from the group of cosolvents and/or oily excipients.
41. The antiparasitic composition according to items 1 to 27, comprising of consisting of 0.1% w/v to 5% w/v ivermectin, F6H8 and one or more excipients selected from the group of cosolvents and/or oily excipients.
42. A method for large-area application of an antiparasitic composition to the skin, comprising topically administering an antiparasitic composition according to any of the items 1 to 27 or 39 to 42 by non-touch application to the target skin area.
43. The method according to item 42, wherein the composition is effective to cover at least 0.5 cm2 of the target skin area per microliter of the composition applied by non-touch application.

The following examples serve to illustrate the invention; however, these are not to be understood as restricting the scope of the invention.

EXAMPLES

Example 1

Preparation of a Solution of Permethrin 5% w/v in F4H8.

250 mg permethrin (Dr. Reddy's, Ph.Eur. grade, cis:trans 25:75) is weighed in a 5-ml volumetric flask; the flask is then filled to 5 ml with F4H8 (Novaliq, purity >99%), closed and shaken at 280 rpm, RT for 16 h. The resulting 50 mg/ml solution appears clear.

Example 2

Preparation of a Solution of Crotamiton 10% w/v in F6H8

500 mg crotamiton (SynTech, Ph.Eur. grade) is weighed in a 5-ml volumetric flask; the flask is then filled to 5 ml with F6H8 (Novaliq, purity >99%), closed and shaken for 5 min at 280 rpm, RT. The resulting 100 mg/ml solution appears clear.

Example 3

Preparation of a Solution of Benzylbenzoate in F4H5

500 mg benzyl benzoate (Symrise, puritiy >99%) is weighed in a 5-ml volumetric flask; the flask is then filled to 5 ml with F4H5 (Novaliq, purity >99%), closed and shaken for 5 min at 280 rpm, RT. The resulting 100 mg/ml solution appears clear.

Example 4

Following the procedure described in the Examples 1 to 3, the following solubility tests were carried out, as shown in Table 1, Table 2 and Table 3.

TABLE 1

Permethrin solubility tests

| Solvent | Solubility (% w/v) |
|---|---|
| F6H8 | 3.9% |
| F4H5 | 4.9% |
| F4H8 | 10.1% |
| 10% MCT in F6H8 | 4.8% |

TABLE 1-continued

| Permethrin solubility tests | |
|---|---|
| Solvent | Solubility (% w/v) |
| 10% MCT in F4H5 | 6.9% |
| 10% paraffin oil in F6H8 | 4.0% |
| 10% paraffin oil in F4H5 | 7.4% |
| F6H8-ene | 5.5% |
| F6H2 | 0.42% |

TABLE 2

| Crotamiton solubility tests | |
|---|---|
| Solvent | Solubility (% w/v) |
| F6H8 | >12% |
| F4H5 | >12% |
| F6H2 | ~6% |

TABLE 3

| Benzylbenzoate solubility tests | |
|---|---|
| Solvent | Solubility (% w/v) |
| F6H8 | 9-10% |
| F4H5 | 11-11.5% |

The invention claimed is:

1. An antiparasitic composition formulated for topical application to the skin consisting of crotamiton, a semifluorinated alkane, optionally a co-solvent, and optionally an oily excipient, wherein the composition is a liquid solution, and wherein the co-solvent is selected from the group consisting of isopropanol, ethanol, liquid medium chain triglycerides, N-methyl-2-pyrrolidone, diethylene glycol monomethyl ether, diethylene glycol monoethyl ether, ethyl acetate, ethyl oleate, octyldodecanol, and diethyl sebecate; and wherein the oily excipient is selected from the group consisting of squalane, silicone oils, mineral oils, essential oils, and liquid triglycerides.

2. The antiparasitic composition of claim 1, wherein the co-solvent is selected from the group consisting of isopropanol, ethanol, liquid medium chain triglycerides, diethylene glycol monoethyl ether, and diethyl sebacate.

3. The antiparasitic composition of claim 1, wherein the oily excipient is selected from the group consisting of squalane, mineral oil, and liquid triglycerides.

4. The antiparasitic composition of claim 1, wherein the crotamiton is present in an amount up to 5% w/v of the composition, and wherein the semifluorinated alkane is F6H8.

5. The antiparasitic composition of claim 4, wherein the crotamiton is present in an amount up 0.1% w/v to 5% w/v of the composition.

6. The antiparasitic composition according to claim 1, wherein the composition is applied in the form of a wipe, a dropper, a roll-on, or a spray.

7. The antiparasitic composition according to claim 1, wherein the composition consists of crotamiton, a semifluorinated alkane, a co-solvent, and optionally an oily excipient, wherein the co-solvent is selected from the group consisting of isopropanol, ethanol, liquid medium chain triglycerides, N-methyl-2-pyrrolidone, diethylene glycol monomethyl ether, diethylene glycol monoethyl ether, ethyl acetate, ethyl oleate, octyldodecanol, and diethyl sebecate.

8. The antiparasitic composition according to claim 7, wherein the semifluorinated alkanes is F6H8.

9. The antiparasitic composition according to claim 1, wherein the composition consists of crotamiton, a semifluorinated alkane, optionally a co-solvent, and an oily excipient, wherein the oily excipient is selected from the group consisting of squalane, silicone oils, mineral oils, essential oils, and liquid triglycerides.

10. The antiparasitic composition according to claim 9, wherein the semifluorinated alkanes is F6H8.

11. The antiparasitic composition according to claim 1, wherein the composition consists of crotamiton, a semifluorinated alkane, a co-solvent, and an oily excipient, wherein the co-solvent is selected from the group consisting of isopropanol, ethanol, liquid medium chain triglycerides, N-methyl-2-pyrrolidone, diethylene glycol monomethyl ether, diethylene glycol monoethyl ether, ethyl acetate, ethyl oleate, octyldodecanol, and diethyl sebecate, and wherein the oily excipient is selected from the group consisting of squalane, silicone oils, mineral oils, essential oils, and liquid triglycerides.

12. The antiparasitic composition according to claim 11, wherein the semifluorinated alkanes is F6H8.

13. The antiparasitic composition according to claim 11, wherein the wherein the co-solvent is selected from the group consisting of isopropanol, ethanol, liquid medium chain triglycerides, diethylene glycol monoethyl ether, and diethyl sebecate, and wherein the oily excipient is selected from the group consisting of squalane, mineral oil, and liquid triglycerides.

14. The antiparasitic composition according to claim 1, wherein the semifluorinated alkanes is F6H8.

15. The antiparasitic composition according to claim 1, wherein the composition is configured to cover area of the skin of at least 0.5 square centimeters per microliter, when applied by non-touch application.

16. The antiparasitic composition according to claim 1, wherein the composition consists of crotamiton, a semifluorinated alkane, and a co-solvent selected from isopropanol and ethanol.

17. The antiparasitic composition of claim 16, wherein the crotamiton is present in an amount up to 5% w/v of the composition, and wherein the semifluorinated alkane is F6H8.

18. A method of treating a parasitic infestation comprising topically administering the antiparasitic composition according to claim 1 to the skin of a subject in need thereof.

19. The method according to claim 18, comprising topically administering the composition by non-touch application.

20. The method according to claim 18, wherein the composition is topically administered by a spray-dispenser, a roll-on dispenser, or a dropper.

21. The method according to claim 18, wherein the parasitic infestation is selected from a mite infestation, a lice infestation, a flea infestation, and a tick infestation.

22. The method according to claim 21, wherein the parasitic infestation is selected from scabies, head lice, body lice, lice of the eyelashes, lice of the eyebrows, mites of the eyelashes, or mites of the eyebrows.

23. The method according to claim 18, wherein the composition is configured to cover area of the skin of at least 0.5 square centimeters per microliter when applied by non-touch application.

24. A method of topical application of an antiparasitic composition comprising applying with a wipe, a roll-on dispenser, a spray dispenser, or a dropper, an antiparasitic composition as defined in claim 1 to the skin of a subject in need thereof.

25. The method according to claim 24, wherein the composition is applied by non-touch application.

26. The method according to claim 24, wherein the composition is administered to a large-area of the skin.

27. The method according to claim 24, wherein the composition is administered by a roll-on dispenser or by a spray dispenser.

28. A kit comprising (a) an antiparasitic composition according to claim 1, and (b) a wipe, a spray dispenser, a roll-on dispenser, or a dropper.

29. A method for large-area application of an antiparasitic composition to the skin, comprising topically administering an antiparasitic composition according to claim 1 by non-touch application to the target skin area.

30. The method according to claim 29, wherein the composition is effective to cover at least 0.5 square centimeters of the target skin area per microliter of the applied composition.

* * * * *